(12) United States Patent
Yi et al.

(10) Patent No.: US 9,412,252 B2
(45) Date of Patent: Aug. 9, 2016

(54) UNIVERSAL FALL DETECTION SYSTEM

(71) Applicants: Ge Yi, San Ramon, CA (US); Dujiang Wan, Fremont, CA (US)

(72) Inventors: Ge Yi, San Ramon, CA (US); Dujiang Wan, Fremont, CA (US)

(*) Notice: Subject to any disclaimer, the term of this patent is extended or adjusted under 35 U.S.C. 154(b) by 0 days.

(21) Appl. No.: 14/161,695

(22) Filed: Jan. 23, 2014

(65) Prior Publication Data

US 2015/0206410 A1    Jul. 23, 2015

(51) Int. Cl.
| | |
|---|---|
| G08B 21/04 | (2006.01) |
| H01H 35/14 | (2006.01) |
| G01P 15/135 | (2006.01) |
| A61B 5/11 | (2006.01) |
| G08B 25/08 | (2006.01) |
| G08B 25/10 | (2006.01) |

(52) U.S. Cl.
CPC .......... *G08B 21/0446* (2013.01); *A61B 5/1116* (2013.01); *A61B 5/1117* (2013.01); *G01P 15/135* (2013.01); *G08B 25/08* (2013.01); *G08B 25/10* (2013.01); *H01H 35/14* (2013.01)

(58) Field of Classification Search
CPC .. A61B 5/1116; A61B 5/1117; G01P 15/135; H01H 35/14

USPC .............. 340/573.1, 665; 73/65.01; 600/300, 600/301, 587

See application file for complete search history.

(56) References Cited

U.S. PATENT DOCUMENTS

| | | | |
|---|---|---|---|
| 6,290,658 B1* | 9/2001 | Kolich | A61B 5/1116 600/595 |
| 6,612,157 B2* | 9/2003 | Urano et al. | 73/65.01 |
| 8,529,448 B2* | 9/2013 | McNair | 600/301 |
| 9,153,114 B2* | 10/2015 | Yi | G08B 21/0446 |
| 2010/0253530 A1* | 10/2010 | Pan et al. | 340/665 |
| 2010/0286567 A1* | 11/2010 | Wolfe et al. | 600/587 |
| 2011/0245731 A1* | 10/2011 | Chiba et al. | 600/587 |
| 2012/0101411 A1* | 4/2012 | Hausdorff | A61B 5/1117 600/595 |
| 2012/0191405 A1* | 7/2012 | Molyneux | G01S 13/82 702/141 |
| 2015/0204647 A1* | 7/2015 | Yi | A61B 5/1117 324/207.17 |

* cited by examiner

*Primary Examiner* — John A Tweel, Jr.

(57) ABSTRACT

A universal fall detect system and its unique designed sensor as well as methodology to detect the fall event are disclosed. The fall event is detected by measuring relative position, and/or orientation between host body and direction of gravity at the spot where falling event happens. The system can present either as a standalone system or a built-in component with supporting software installed on other devices. The system linked to wide network and wide audience can trigger several emergency response and assistances if needed in time when a falling event happens.

28 Claims, 10 Drawing Sheets

FIG. 8 ures are disclosed in this invention.
UNIVERSAL FALL DETECTION SYSTEM

FIELD OF INVENTION

The invention is related to fall detection and response system, and more particularly, to use sensor system to detect the fall of host based on relative position/orientation between host body and direction of gravity at the spot where a falling event happens.

BACKGROUND ART

Fall detection is very important and has widely applications in older care, patient care, child care, disable care as well as safety for outdoor sports even. To develop a reliable fall detection system has huge market potential and great society impact.

Conventional fall detection system is designed to detect whether a real fall event happens by matching falling acceleration data with pre-set models or thresholds using enormous different kinds of algorithm. However, a random fall event depends on actual situation and prior falling movement of the host. It is so complicated that it is almost impossible to have a precise model to mimic the real event. Despite of great efforts, there is no a successful product existing on the market with great impact. The present invention resolves this dilemma by directly measuring/sensing the relative position/orientation between the host body and direction of gravity at the spot where a falling event happens.

SUMMARY OF THE INVENTION

A universal fall detection system in form of, either an independent portable device or built-in component in smart phone, or tablet, or other portable device such as Google glass, etc., is disclosed. The core of the system is a sensor subsystem, which senses the relative orientation/position of the host body with the direction of the gravity at the spot to detect whether a falling event happens.

Several alternative designs of sensor sub-system as well as a system and method to make the universal fall detection miniature system-on-chip devices in large volume manufacture environment are disclosed in this invention.

DETAILED DESCRIPTION

The following description is provided in the context of particular designs, applications and the details, to enable any person skilled in the art to make and use the invention. However, for those skilled in the art, it is apparent that various modifications to the embodiments shown can be practiced with the generic principles defined here, and without departing the spirit and scope of this invention. Thus, the present invention is not intended to be limited to the embodiments shown, but is to be accorded the widest scope consistent with the principles, features and teachings disclosed here.

Figure 1:
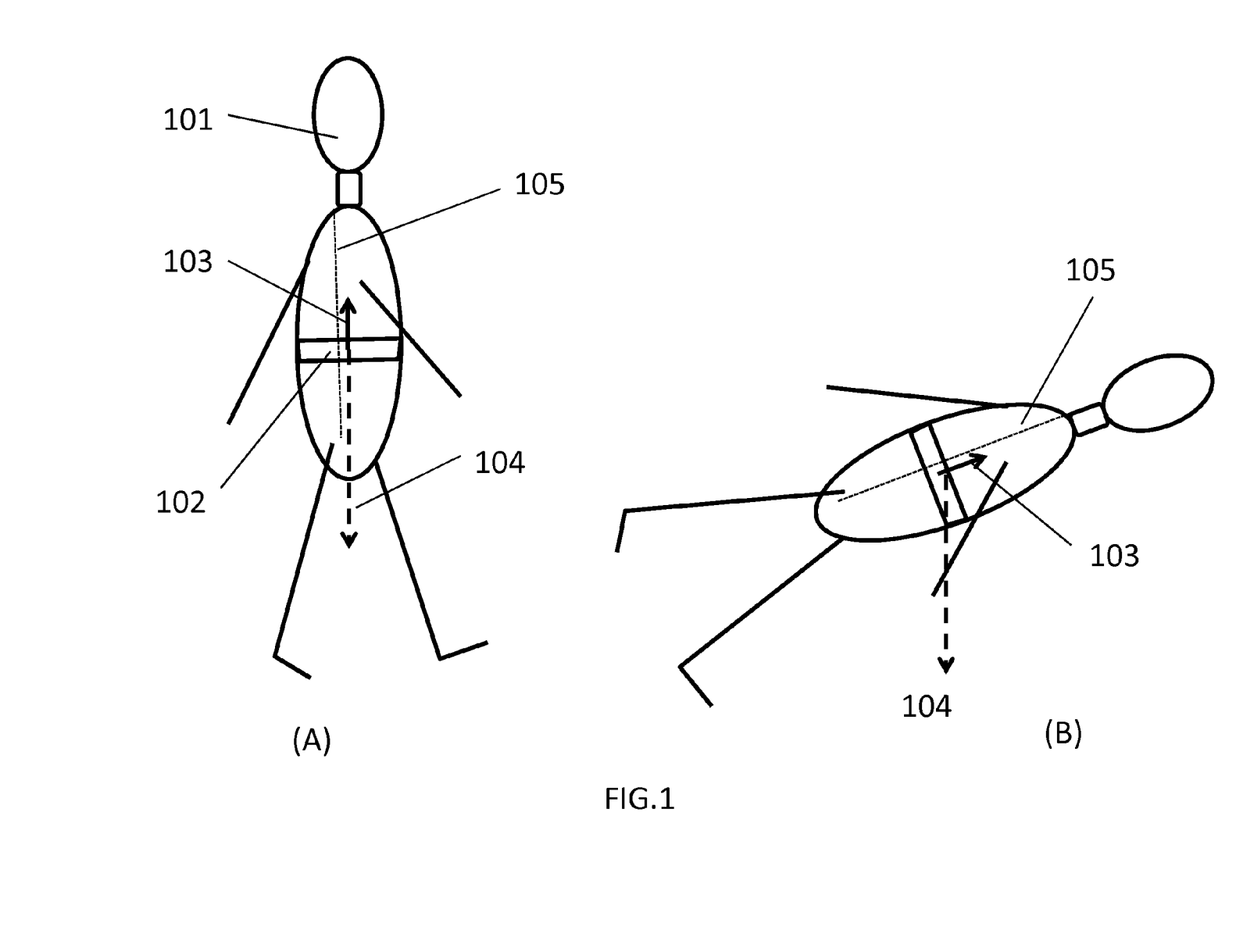
FIG. 1 illustrates the detection mechanism of the proposed universal fall detection system by sensing the relative position or orientation of host body with the direction of gravity at the event of fall: (A) Normal body orientation before fall; (B) body orientation after fall.

FIG. 1 illustrates the detection mechanism of the proposed universal fall detection system by sensing the relative position or orientation of host body with the direction of gravity at the event of fall. The host can be anything such as a human, a robot, or a vehicle, whose fall is our major concern. The orientation of the host's body center-line can be used as a general reference for the body orientation of the host. In the particular scenario described here, the host is a human 101, whose spine 105 is used as a reference for the orientation of the human body. FIGS. 1 (A) and (B) describes the situations before and after fall happens, respectively. It is quite noticeable that, regardless of the details of how the fall happens and the details of the speed or the acceleration before and after fall, the direction of local gravity 104 is not changed. However, the relative orientation between the host body (105) and direction of gravity (104), shown here as the angle between 105 and 104, has changed after fall happens. It would be extremely reliable for the universal fall detection system to sensor only the change of the angle between 105 and 104 and ignore the details happened during the fall event. In FIG. 1, a fall detection system in form of a belt 102 is worn on the waist of human body. The relative orientation between the universal fall detection system indicated here as an up-pointing arrow 103 and the human body 105 is kept without change before and after fall as shown here in FIGS. 1 (A) and (B). The proposed universal fall detection system is designed to detect the change of the angle between the host body 105 and direction of local gravity 104.

Figure 2:
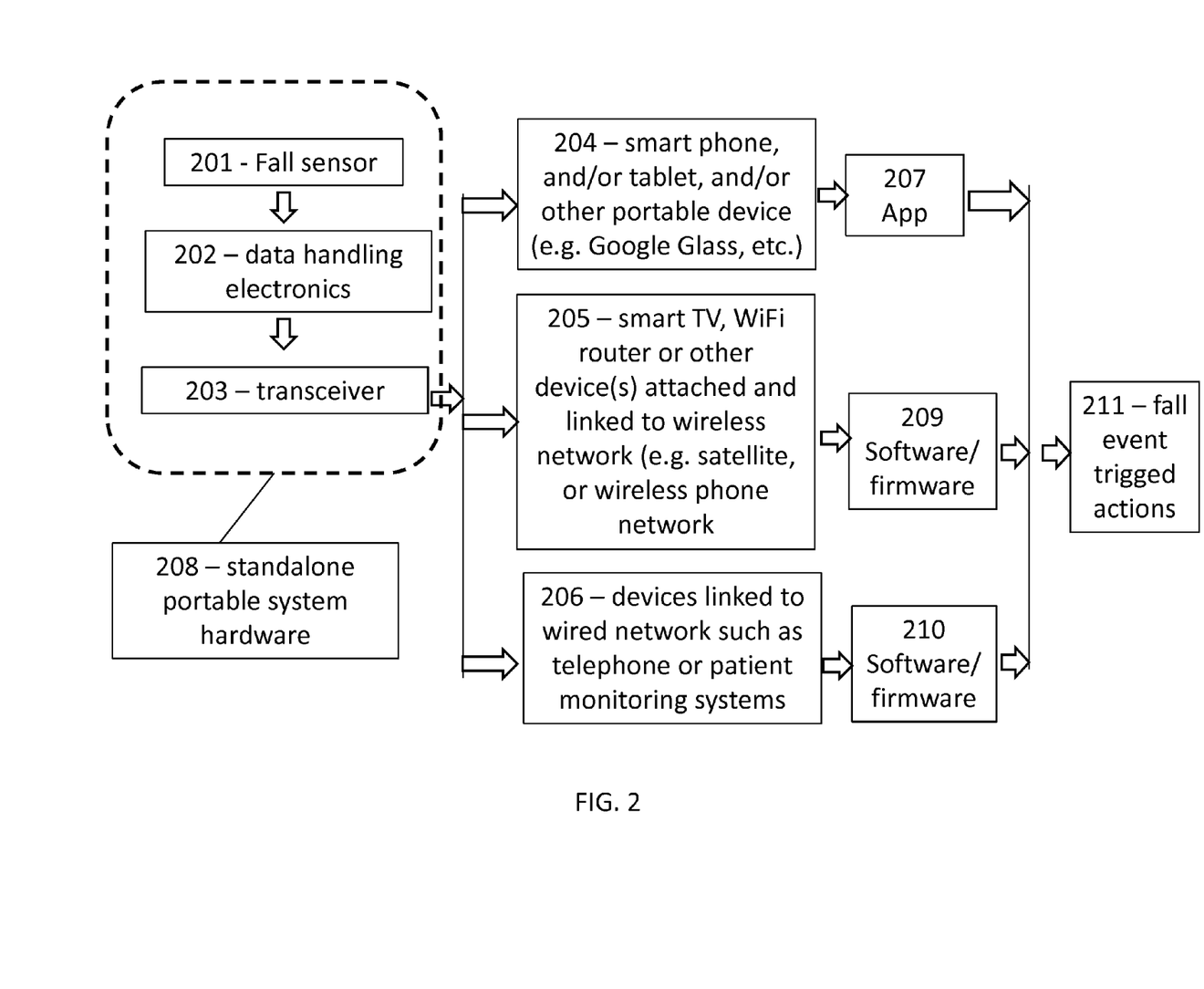
FIG. 2 illustrates the information or data flow for standalone portable fall detection system.

FIG. 2 illustrates the information or data flow for the proposed standalone fall detection system. The fall sensor 201 continuously monitors the relative orientation between the host body 105 and local gravity direction 104 shown in FIG. 1. The electrical signal from the fall sensor 201 is analyzed by the data handling electronic 202. When a falling signal is received, the data handling electronic 202 first analyzes whether the event indeed happens, and then sends out a fall-SOS signal to either 204 (smart phone/tablet/other portable device, such as Google glass, etc.); or/and 205 (internet ready TV, WiFi router, or other wireless network ready devices, which is attached and linked to wider network); or/and 206 (devices linked to wired network such as telephone or patient monitoring system) for emergency help by transceiver or transmitter 203 when a falling event is confirmed. Devices 204, 205, and 206 with their installed respective application software (app) 207, software/firmware 209, and software/firmware 210 act as information distribution gateway to a wide network. For example, the app 207 initiates 204 to send notification call(s) or fall-SOS call(s) to pre-configured call list; and/or to switch on the voice recording function equivalent to black-box on the plane; and/or to turn on the GPS location function for a three parties to track the location of the host. In this example, the hardware of portable system 208 comprises the fall sensor 201, the data handling electronics 202 and transceiver or transmitter 203. The described universal fall system consists with hardware 208 as well as software 207, 209 and 210.

As a simplified version of standalone portable system 208, a wire connection system can be used to replace transceiver or transmitter 203 in order to make the communication between 208 and 204.

Figure 3A:
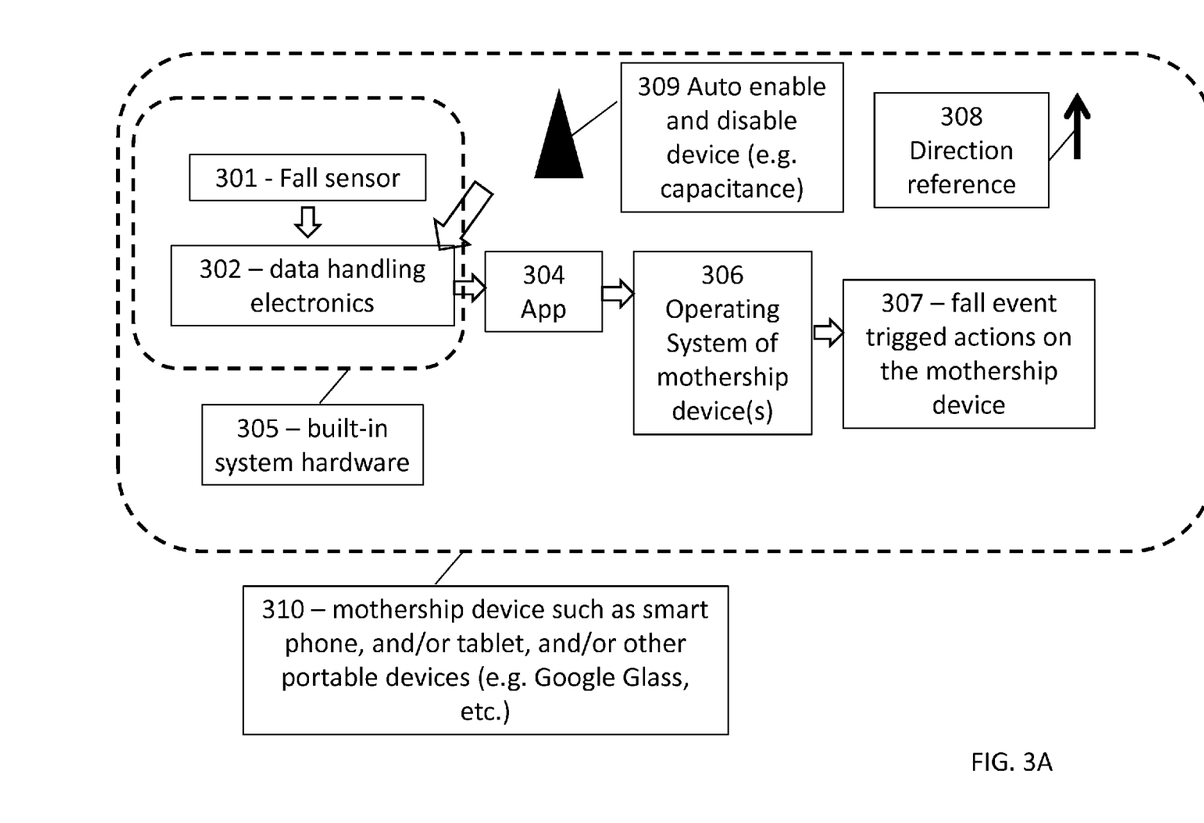
FIG. 3A illustrates the information or data flow for a fall detection system built as a component in a mothership device.

FIG. 3A illustrates the information or data flow for a universal fall detection system built as a component in a mothership device. In this particularly embodiment, the built-in system hardware 305 comprises fall sensor 301 and data handling electronics 302, which are built as a component in a mothership device 310, such as smart phone, or tablet, or other portable devices e.g. Google glass. The fall sensor 301 continuously monitors the relative orientation between the host body 105 and local gravity direction 104 shown in FIG. 1. The electrical signal from the fall sensor 301 is analyzed by the data handling electronic 302. When a falling signal is received, and a falling event is confirmed by data handling electronics 302, a fall-SOS will be generated by data handling electronics 302, and sent to mothership devices through the associated application software (app) 304, which communicates to operating system 306 (OS such as iOS, Android, Window 8, and Chrome) on the mothership devices. The fall-SOS signal will initiate necessary emergency actions such as sending notification call(s); fall-SOS call(s) to pre-configured call list; switching on the voice recording function equivalent to black-box on the plane; and/or turning on the GPS function for a three parties to track the host location.

In the built-in system, the fall sensor in the mothership device 310 needs to align to the host's centerline. The alignment is kept without change before and after fall. A reference 308 (shown here as arrow) in FIG. 3A is a simple marker on 310 to indicate the alignment direction. The fall detection function can be enabled or disabled in App 304 manually. An auto switching device (sensor) is integrated in 310 to enable or disable the fall detection function.

Figure 3B:
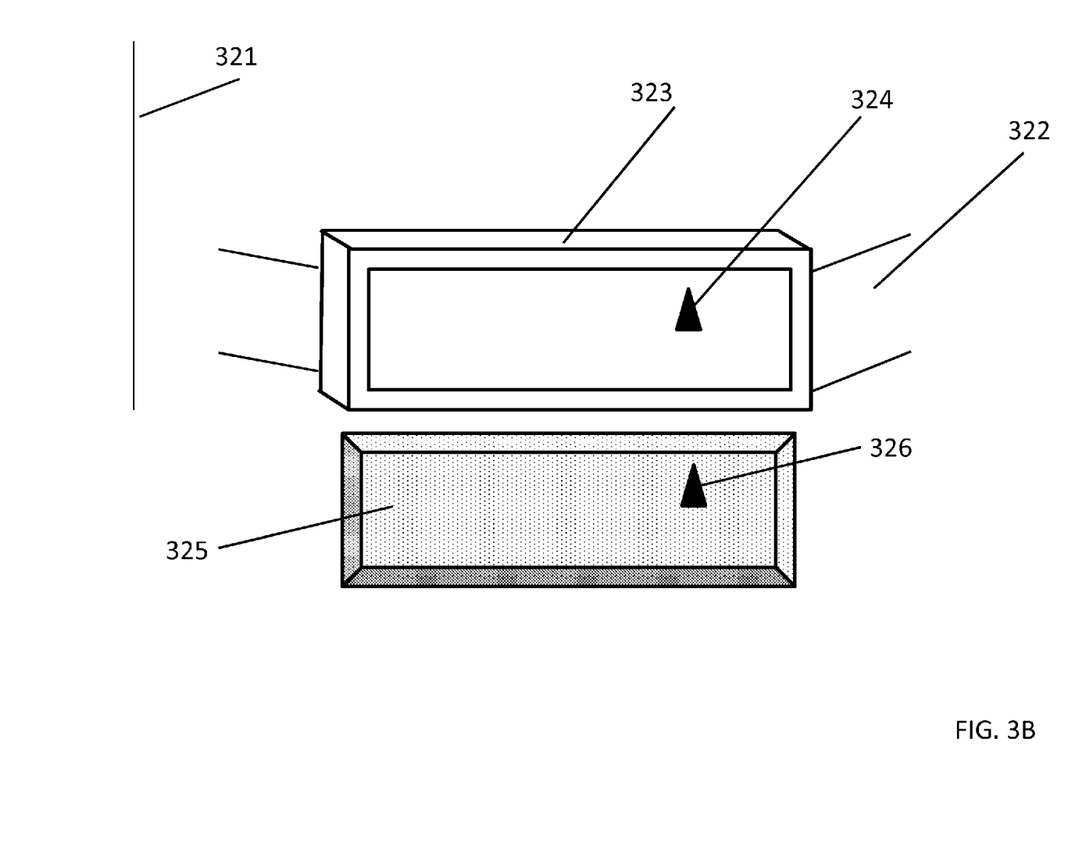
FIG. 3B illustrates one of the embodiments for auto switching design (auto enable and disable device 309 shown in FIG. 3A).

FIG. 3B further illustrates one of the auto switching designs 309 in FIG. 3A. An accessory 323 (shown here as smartphone carrying case) coming along with portable device 325 (shown here as a smartphone) is worn on a belt 322 around the host's waist. Line 321 indicates their alignment direction (the host, the accessory and the portable device). The matching feature 324 built on the carrying case 323 and its counterpart 326 built (shown in FIG. 3A as 309) on the portable device 325 together play the switching function. When the two pair of 324 and 326 is matched, and aligned correctly, it will trigger the data handling electronics 302 in FIG. 3A to enable the fall detection of the system 305, and send a detection-on notice to App 304 by either voice or a beep. There are lots of choices on how to make this pairing feature 324 and 326 to fulfill enable/disable function. For an example, a capacitor switching sensor can be built on 325 and 323 by two thin metal pads representing 324 and 325 features. The two metal pads are covered with dielectric materials. A pre-set of the capacitance threshold value is used to control the enable or disable of the fall detection function. When 323 and 325 attach each other correctly, the capacitance will be above the preset threshold, and the fall detection function will be turned on automatically. In the case of 323 and 325 detaching each other or attaching each other incorrectly, the capacitance drops below the preset threshold, the fall detection function will turn off immediately.

Figure 4:
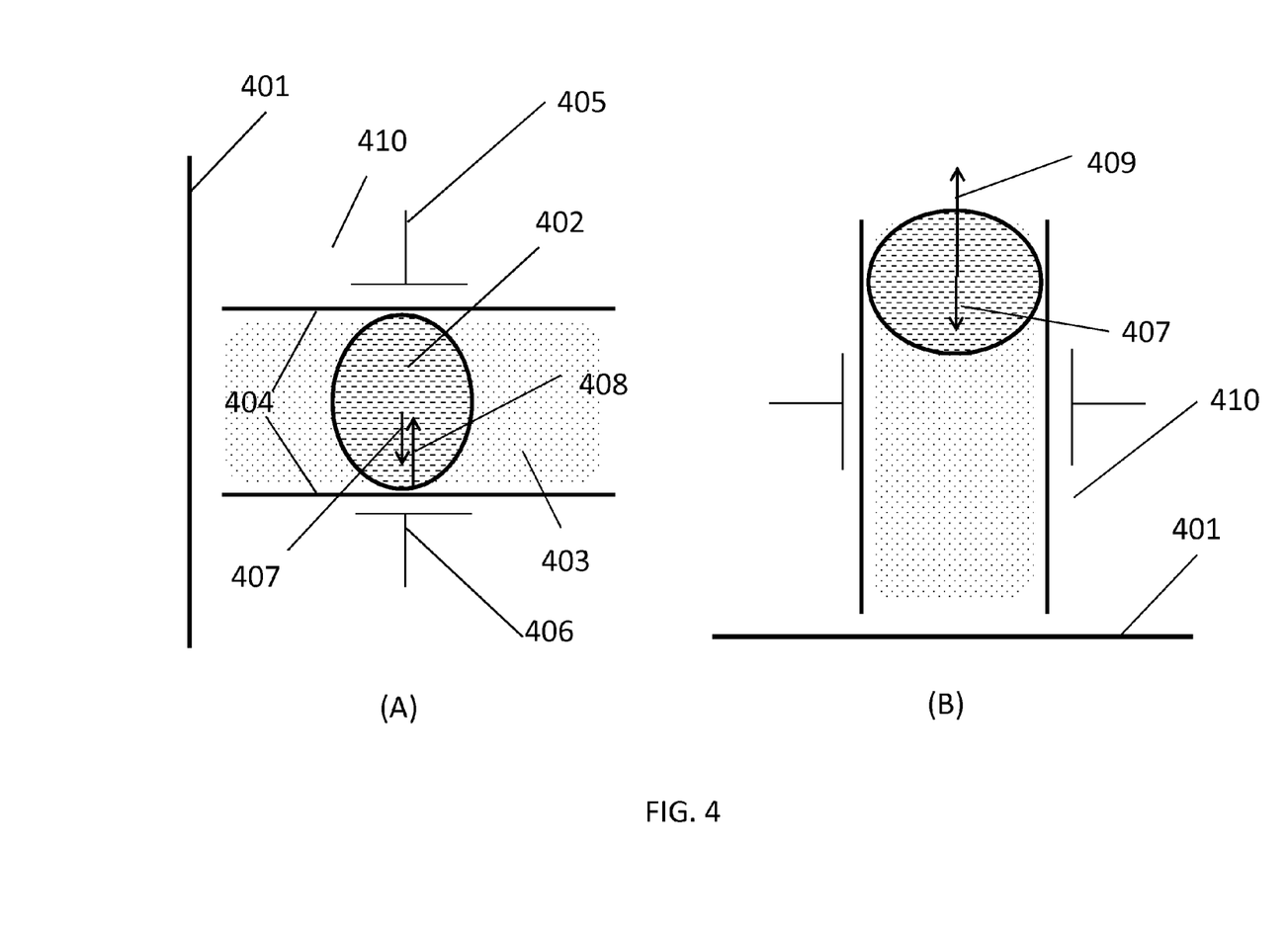
FIG. 4 illustrates one of the embodiments for detecting relative orientation change between the host body and direction of gravity with a sensor fixed on host body.

FIG. 4 illustrates one of the falling sensor designs to detect the change of the relative orientation between the host body 105 and direction of gravity 104 shown in FIG. 1. FIG. 4(A) and FIG. 4(B) represent the scenarios before and after fall. It is noticeable that body centerline 401 and the centerline of the sensor 410 are always parallel to each other without any change before and after fall. The sensor 410 has a dielectric tube container 404, in which two kinds of non-intermixable medium 402 and 403 with different densities present. Both medium 402 and 403 can move inside the tube. Medium 402 is a minority, whose position along the tube can be detected by a sensing pair 405 and 406. When the tube 404 is at horizontal position shown in FIG. 4(A), the gravity 407 of the minority medium 402 will be balanced by the supporting force 408 from the tube 404, and the medium 402 sits between the pair 405 and 406. Any titling away from the horizontal position of the tube 404 drives the medium 402 moving away from its initial position between 405 and 406 shown in FIG. 4B due to the imbalance of forces between the gravity 407 and buoyancy 409 provided by medium 403. The medium 402 will moves up as shown in FIG. 4(B) if its density is less than that of medium 403, otherwise, it will drop to the bottom of the tube. The medium 402 and 403 can be gas and liquid (e.g., air bubble and liquid spirit), respectively; or two kinds of non-intermixable liquids (e.g., oil droplet and water); or one solid particle and one liquid (e.g., wooden beam and water), respectively.

One example of this kind of system is a lever, which has an air bubble floating in liquid spirit. A human being can use the eyes to check whether the air bubble stays in the middle of transparent container to decide whether it sits horizontally or not. A sensing pair in this invention is used to automatically detect the tube tilting status. A pair of metal electrodes 405 and 406 together forms a capacitor. The moving of medium 402 along the tube due to its tilting will change the capacitor's capacitance. Hence, the capacitance is a function of the tube tilting angle, and it can be used to sense a falling event by detecting the directional change of the gravity 407 respect to its own body 401.

Alternatively, the pair of laser emitter 405 and laser detector 406 can be chosen to sense the tube tilting status. The moving of medium 402 along the tube due to its tilting will change the laser light transmission intensity. The change of the laser light transmission intensity detected by laser detector 406 will be a function of the change of the sensor tube tilting angle. Hence, it can be used to sense a falling event by detecting the directional change of the gravity 407 respect to its own body 401.

The miniaturized universal falling system, a few mm for example, can be made in large volume using semiconductor wafer process together with the methods of microfluidic device fabrication. The two intermixable medium can be chosen in such a way that it can detect the final status but much less sensitive than the normal lever we use in our ordinary life. Although there is only one sensing pair shown here in the drawing, several sensing pairs can be arranged along the tube to determine how much change of the angle between the host body and local gravity as well as how fast this change happens.

Figure 5:
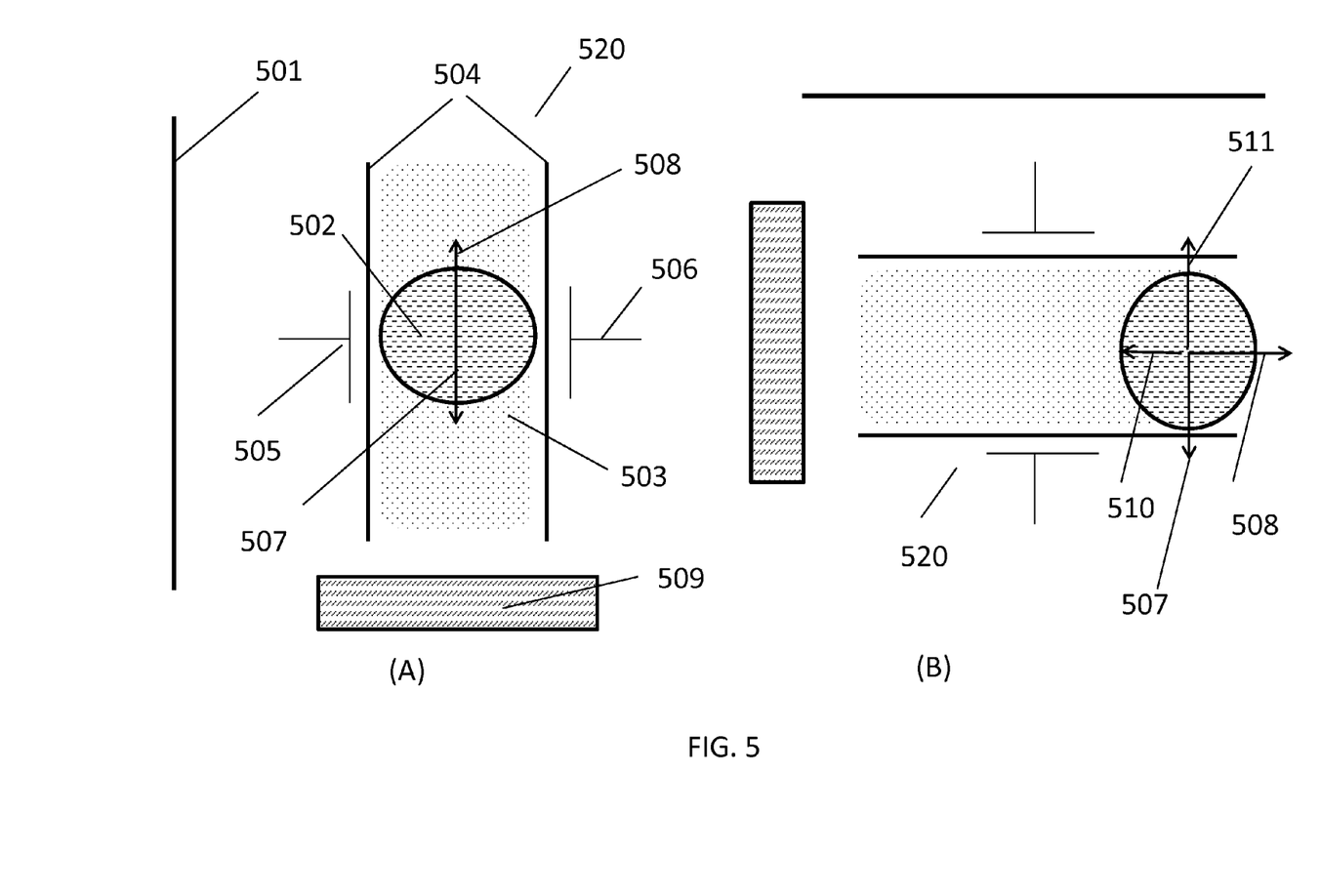
FIG. 5 illustrates one of the embodiments for detecting relative orientation change between the host body and direction of gravity with a sensor fixed on host body.

FIG. 5 illustrates another of the falling sensor designs to detect the change of the relative orientation between the host body 105 and direction of gravity 104 shown in FIG. 1. The concept of the design shown in FIG. 5 is similar to that shown in FIG. 4, but the minority medium 502 floating in the medium 503 shown in FIG. 5(A) is supported by the external force 508 provided by the third party 509, not the buoyancy provided by the medium 503 itself. The medium 503 can be gas, liquid, or even vacuum. The minority medium 502 is a solid particle floating in the medium 503 (gas, liquid, or vacuum). The external force can be magnetostatic force, electrostatic force or other long distance force interacting between the minority medium 502 and external object 509.

FIG. 5(A) and FIG. 5(B) represent the scenarios before and after fall. The direction of the external force 508 is always parallel to the body centerline 501 before and after fall. As shown in FIG. 5(A), the gravity 507 of the minority medium 502 is balanced by the external force 508 provided by the third part 509 when the tube 504 is at vertical position before fall. Initially, the minority medium 502 position in the medium 503 is at the site between the sensor pair 505 and 506. Any tilt of the tube 504 from vertical position breaks the balance between the gravity 507 and the external force 508, resulting in the minority medium 502 moving away from its initial position as shown in FIG. 5B. Under any normal circumstance, the friction force 510, which is proportional to the force 511 normal to the wall of tube 504, is negligible comparing its magnitude with the driving force. A pair of metal electrodes 505 and 506 together forms a capacitor. The moving of medium 502 along the tube due to its tilting will change the capacitor's capacitance. Hence, the capacitance is a function of the tube tilting angle, and it can be used to sense a falling event by detecting the directional change of the gravity 507 respect to its own body 501.

Alternatively, the pair of laser emitter 505 and laser detector 506 can be chosen to sense the tube tilting status. The moving of medium 502 along the tube due to its tilting will change the laser light transmission intensity. The change of the laser light transmission intensity detected by laser detector 506 will be a function of the change of the sensor tube tilting angle. Hence, it can be used to sense a falling event by detecting the directional change of the gravity 507 respect to its own body 501. More sophistic sensing approach can be adopted, which will be given later.

The miniaturized universal falling system shown here, even below 1 mm, can be made in large volume using semiconductor wafer process together with the methods of microfluidic device, and/or MEMS fabrication. Although there is only one sensing pair shown here in the drawing, several sensing pairs can be arranged along the tube to determine how much change of the angle between the host body and local gravity as well as how fast this change happens.

Figure 6:
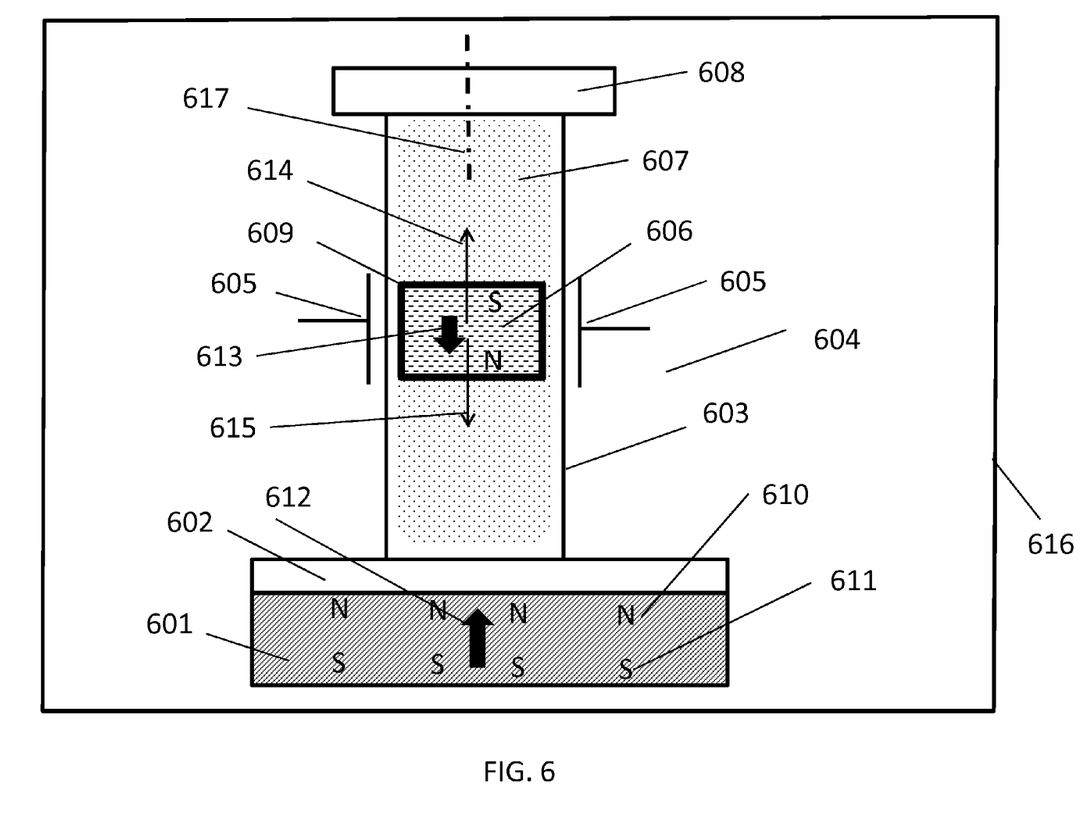
FIG. 6 illustrates a sketched example of one of the detailed designs shown in FIG. 5 and material choice.

FIG. 6 illustrates a sketch of one of the detailed designs shown in FIG. 5 and its material choices. The sensor comprises a bottom permanent magnet 601 (e.g. either a continue magnetic film or patterned magnet); an optional non-magnetic space layer 602; a free space in form of tube 603 made within the dielectric matrix 604; a small permanent magnet 606 floating inside tube 603 with coating layer 609 for reducing the friction between the magnet 606 and side wall of tube 603; a lid 608 on top of the tube 603 to prevent the magnet 606 from moving out of the tube 603 when fall happens; and a pair of electrodes 605, which forms a capacitance sensor and locates in the equilibrium position of magnet 606.

As shown in FIG. 6, the permanent magnet (or magnetic layer) 601 has its magnetization 612 pointing up with north magnetic pole 610 on the top surface and south magnetic pole 611 at the bottom surface, while, on the other hand, the small magnet 606 has its magnetization 613 pointing down with its north magnetic pole at its bottom and south magnetic pole on top. The magnetostatic repelling force 614 on magnet 606 from the permanent magnet 601 provides the magnet 606 supporting to float inside tube 603 before fall against the gravity 615 of the magnet 606 shown in FIG. 6 when the center line 617 of tube 603 parallel to direction of local gravity 615. The capacitance between the pair of electrodes 605 is proportional to $\in A/d$, while A is the facing area of the two electrodes 605, d is the distance of the two electrodes, and E is permittivity of material between the electrodes. Any tilting of the center line 617 away from the vertical direction due to fall will drive the magnet 606 away from its vertical equilibrium position, resulting in the capacitance change between the pair of electrodes 605 due to the change of permittivity E. The capacitance sensor can be used to sense a falling event by detecting the directional change of the gravity 617 respect to the center line 617.

The medium 607 filled inside the tube 603 can be air, a kind of gas, a kind of liquid, or even vacuum. A soft magnetic shield 616 can be built around the sensor in order to eliminate interference or disturbing from any external magnetic field. Multiple pairs of sensor pairs can be made along the tube 603 to precisely sense the magnet 606 moving during the fall, and thus define and characterize the fall. All the structures and features shown here in FIG. 6 can be made by semiconductor process together with MEMS process, which is well known in the field. Therefore, volume manufacture as well as size reduction of the sensor become feasible with low cost.

Figure 7A:
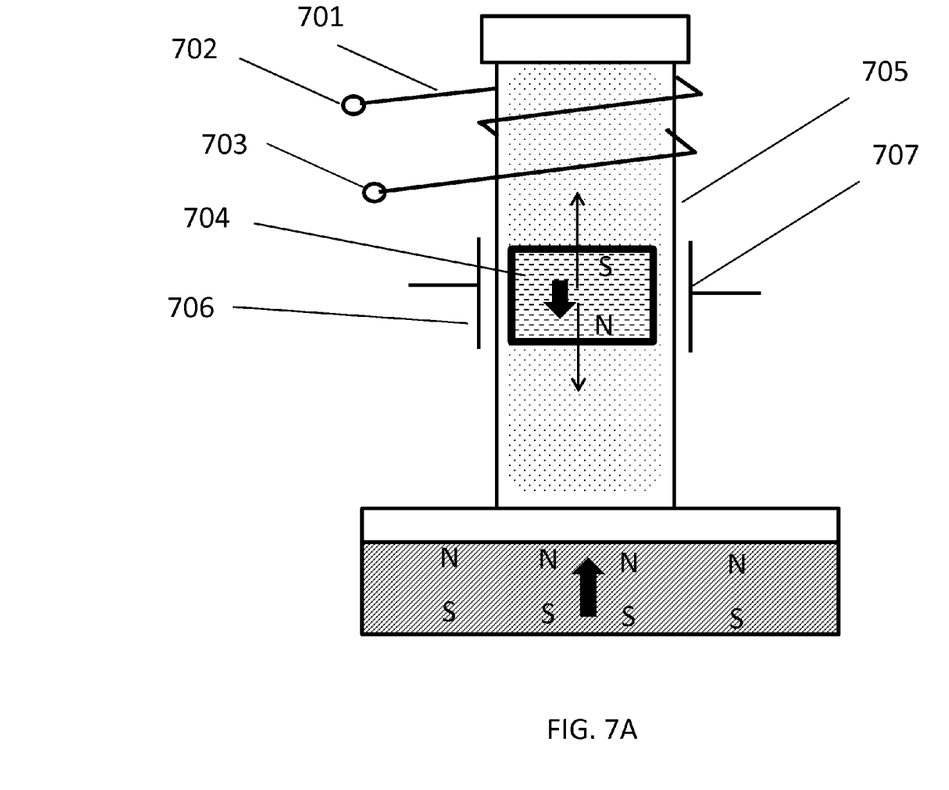
FIG. 7A illustrates one of the embodiments of sensor similar to that shown in FIG. 6 but with additional coil.

FIG. 7A illustrates one of falling sensor designs with a surrounding coil. The sensor has the same structure designs as that shown in FIG. 6 except the surrounding coil to fulfill the same functionalities. The sensor shown in FIG. 7A has additional coil 701 surrounding, locating outside the tube and at one end of the tube. The movement of the floating magnet 704 inside the tube 705 triggered by a fall event will cause the change of the magnetic flux through the coil 701, and an electromotive force (emf) voltage will be built up between the output 702 and 703 according to Faraday's law of induction.

Whenever the output emf voltage between 702 and 703 is below a preset threshold value, it is assumed that the fall event finishes or any possible event which could lead to possible falling has finished. Then the capacitance between the pair of electrodes 706 and 707 is measured to determine whether the floating magnet is still between the electrode pair or not. This information can be used to judge whether the fall indeed happens or not. This approach is certainly the most reliable method to determine and sense the fall as it is only measure the end results—"Does the orientation of the host change respect to the direction of local gravity?"—Which matches the definition of fall. All the structures and features shown here in FIG. 7A can be made by semiconductor process together with MEMS process, which is well known in the field. Therefore, volume manufacture as well as size reduction of the sensor become feasible with low cost.

Figure 7B:
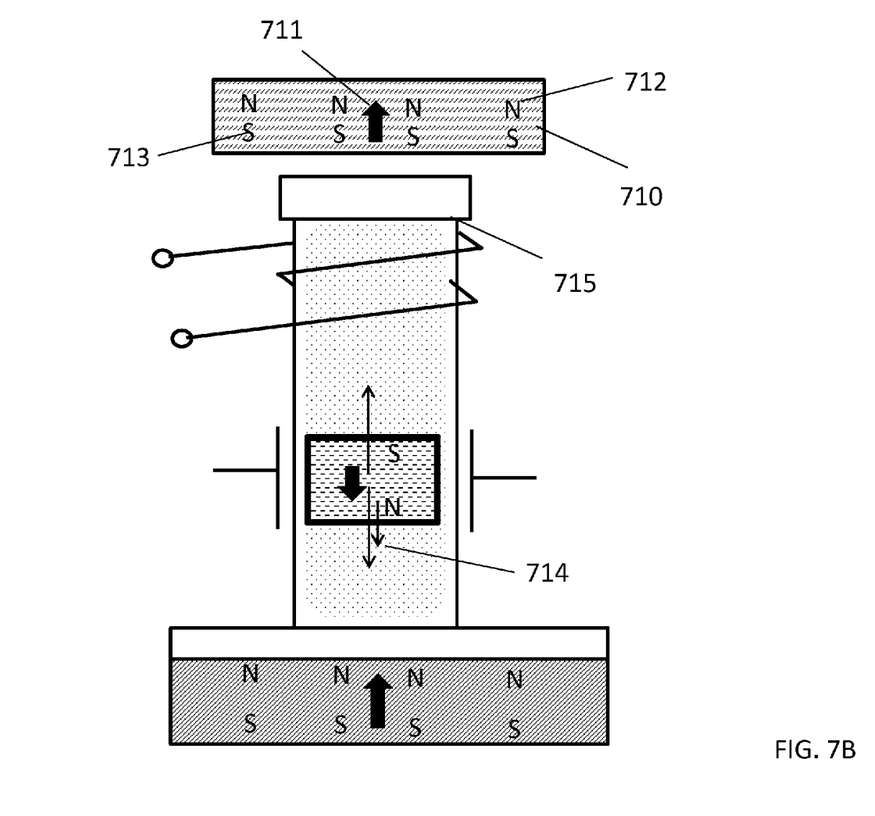
FIG. 7B illustrates one of the embodiments of sensor similar to that shown in FIG. 7A but with additional permanent magnet.

FIG. 7B illustrates one of the embodiments of sensor similar to that shown in FIG. 7A but with additional permanent magnet. The sensor shown in FIG. 7B has additional permanent magnet 710, locating outside the tube and at top end of the tube. Its magnetic north and south poles are at the top and bottom surface of magnet 710, respectively. Hence, the magnetization 711 of permanent magnet 710 is pointing upwards. The magnetostatic force 714 between the magnet 710 and floating magnet 704 shown in FIG. 7A is pointing downwards as shown by the arrow. This kind of design prevents the floating magnet 704 from sticking to the top lid. Moreover, this kind of design also provide extra knobs to tune the sensitivity of the sensor by adjusting the position of position and/or strength of the magnet 710.

Figure 8:
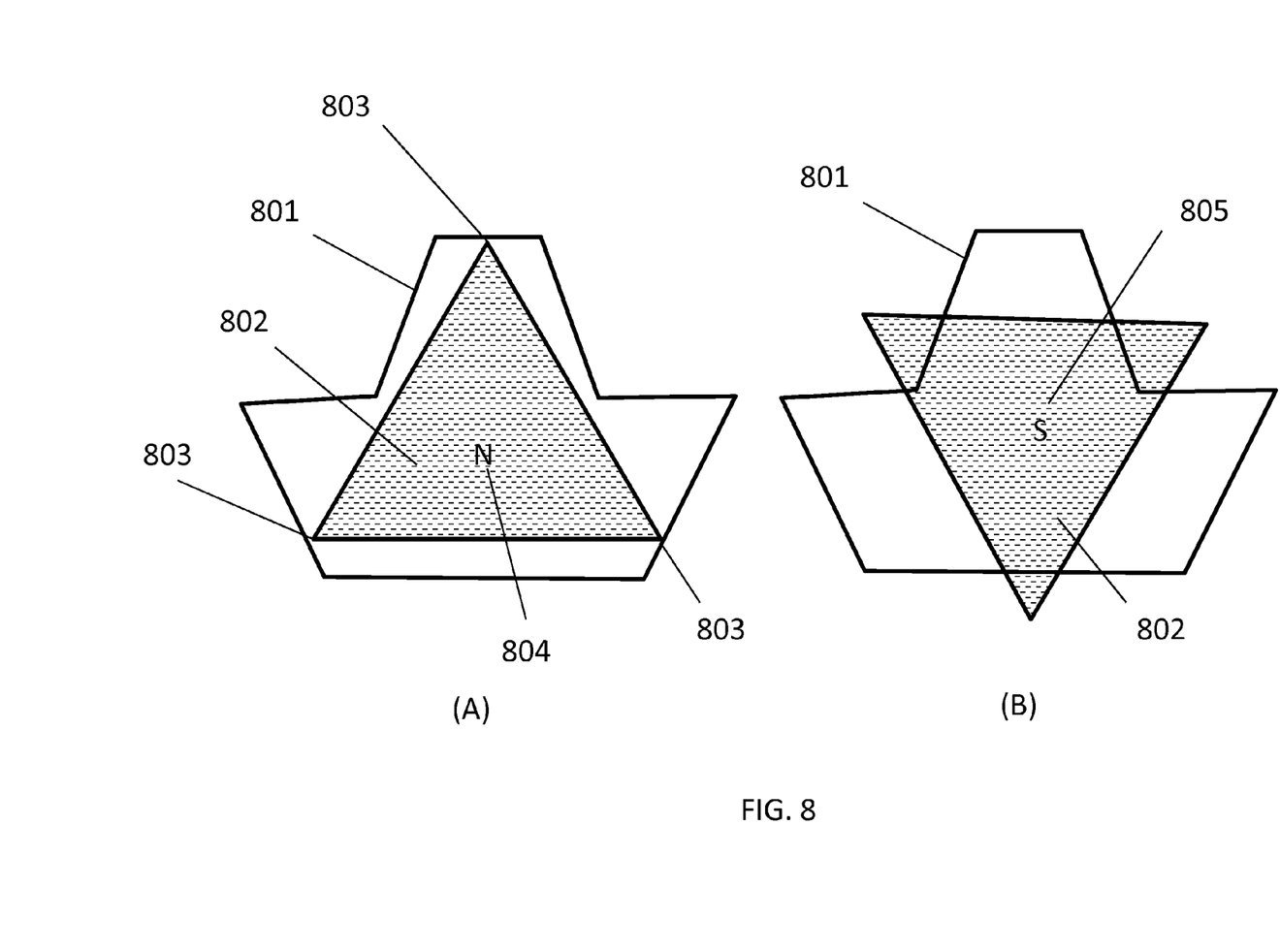
FIG. 8 illustrates one of embodiments or designs of an asymmetric cross section to prevent the flipping of the floating magnet for system shown in FIG. 6 and FIG. 7

In order to avoid the sensor shown in FIG. 6, FIG. 7A and FIG. 7B malfunction, the flipping (or turning up-side-down)

of the floating magnet (magnet 606 in FIG. 6) should be strictly prohibited. On the other hand, to increase the sensitivity of sensor shown in FIG. 6 and FIG. 7, the friction force between the floating magnet and wall of the tube need to be minimized. FIG. 8(A) illustrates one of the embodiment or designs for the cross sections of the tube and floating magnets. 801 is the cross section of the tube, in which the magnet 804 locates, whose magnetic north pole N 804 appears at the top surface. Cross section of 801 is designed in such an irregular or asymmetric shape to ensure that the contact area 803 between the floating magnet 804 and side wall 801 is minimized. FIG. 8 (B) shows that the designs of the shape of side wall 801 and the floating magnet 805 prevents the flip of the magnet 805 by showing that the flipped magnets 805 is not compatible with cross section shape of the side wall of tube.

What is claimed is:

1. A system comprising:
    at least a sensor configured to detect a fall of a host based on a change of relative position, and/or orientation between the host body and gravity where the fall happens;
    at least an information handling subsystem to receive, process and respond to signals from said sensor;
    said sensor comprises:
    at least a two-non-intermixable medium, whose relative location varies depending on its orientation with respect to gravity;
    at least a detection system to detect relative position between said two-non-intermixable medium;
    said two-non-intermixable medium comprises:
    either a kind of liquid and a gas bubble; or two kinds of non-intermixable liquids; or a kind of liquid and a solid with density less than liquid; or a kind of gas (or even vacuum) and a solid floating in gas (or vacuum) supported by at least an external force; or a kind of liquid and a solid, which is denser than liquid, and is floating in liquid supported by at least an external force.

2. The system of claim 1, wherein said system is built as a standalone wearable or a portable system further comprising:
    at least a transceiver, or transmitter, to communicate between said system to an outside device (or devices), which acts (or act) as an distribution gateway for an piece of information or a data package to a wide network and wide audience;
    at least a software installed on said outside device (or devices) to handle and respond to said piece of information or said data package from said system.

3. The wearable or portable system of claim 2, wherein said outside device is a smart phone; or cell phone; or ipod; or a WiFi router; or a receiving device attached to a WiFi route; or a receiving device attached to a wired network; or a tablet; or a telephone.

4. The wearable or portable system of claim 2, wherein said software is an application software (app) at an event of fall, to send a notification call(s) or a SOS call(s) to a pre-configured call list; and/or to switch on a voice recording function on said wearable or portable system; and/or to switch on a location function for a third party (parties) on said wearable or portable system to track said wearable or portable system's location.

5. The system of claim 1, wherein said system is made as a built-in functional component integrated into a smart phone (or/and tablet; or/and other wearable or portable device).

6. The system of claim 5, wherein said built-in functional component has a supporting software, compatible with an operation system (OS) of said smart phone (or/and tablet; or/and other wearable or portable device), at the event of fall, to send a notification call(s) or a SOS call(s) to a pre-configured call list; and/or to switch on a voice recording function; and/or to switch on a location function for a third party (or parties) to track said smart phone (or/and tablet; or/and other wearable or portable device)'s location.

7. The system of claim 1, wherein said external force is a magnetic force between the magnets.

8. The system of claim 1, wherein said external force is an electrostatic force.

9. The system of claim 1, wherein said detection system is based on a capacitance change between two electrodes sandwiching one of said medium.

10. The system of claim 1, wherein said detection system is based on an optical emitter and sensor pair on the two opposite sides of one of said medium.

11. The system of claim 1, wherein said system is built using a monolithic semiconductor wafer process together with a microelectromechanical system (MEMS), or/and microfluidic system wafer process in a volume production environment to achieve an system-on-chip configuration in a miniature form factor.

12. The system of claim 1, wherein said system is built using a system-in-packaging approach.

13. The system of claim 7, wherein said magnetic force is a magnetic force between two hard-magnet containing solid bodies.

14. The system of claim 2, wherein said standalone wearable or portable system is a belt worn around the host's waist, or a decoration feature fixed on the host body, whose relative orientation with the host body does not change in a fall even.

15. The system of claim 1, wherein said system is built as a standalone wearable or portable system further comprising:
    at least a communication port for wire connection between said system and an outside device (or devices);
    at least a software installed on said outside device (or devices) to handle and respond to a piece of information or a data package received from said system.

16. The system of claim 15, wherein said outside device (or devices) is a smart phone, or a cell phone; or an ipod; or another wearable or portable device.

17. The system of claim 5, wherein said smart phone (or/and tablet; or/and other wearable or portable device) has a direction reference drawing or feature on it to indicate the correct orientation respect to the host body.

18. The system of claim 6, wherein said a supporting software has a function to allow a fall detection to be enable or disable.

19. The system of claim 5, wherein said smart phone (or/and tablet; or/and other wearable or portable device) further has an accessory for securely holding and/or fixing said smart phone (or/and tablet; or/and other wearable or portable device) with respect to the host body before and after a fall.

20. The system of claim 5, wherein said smart phone (or/and tablet; or/and other wearable or portable device) further has at least a pairing sensing feature, whose function is to automatically enable or disable of the fall detection function.

21. The system of claim 19, wherein said accessory has at least a complementary pairing feature, which matches said pairing sensing feature on said smart phone (or/and tablet; or/and other wearable or portable device) when a relative position between said accessory and said smart phone (or/and tablet; or/and other wearable or portable device) is correct for enabling a fall detection function of said built-in system.

22. The system of claim 20, wherein said pairing sensing feature is connected to an information handling subsystem to automatically decide whether the correct pairing is done or not.

23. The system of claim 6, wherein said a supporting software has a function to notify the host when the relative position between said accessory and said smart phone (or/and tablet; or/and other wearable or portable device) is correct for enabling said built-in system's fall detection function.

24. The system of claim 19, wherein said accessory is a smart phone carrying case.

25. The system of claim 21, wherein said pairing feature is a metal pad.

26. The system of claim 20, wherein said pairing sensing feature is a metal electrode with a dielectric surface cover-layer connected to an information handling subsystem.

27. The system of claim 26, wherein said metal electrode with a dielectric surface cover-layer pairs with said metal pad to form a capacitance, whose value is used to compare with a preset value or a threshold to decide whether a correct orientation is set for the system's fall detection.

28. The system of claim 1, wherein said system is built as a standalone wearable or portable system further comprising:
   at least a transceiver, or a transmitter, to communicate to a satellite, and/or a cell phone network to allow a piece of information or a data package to distribution to a wide audience.

\* \* \* \* \*